United States Patent [19]
Katz et al.

[11] Patent Number: 6,150,511
[45] Date of Patent: Nov. 21, 2000

[54] CHIMERIC ENZYME FOR PROMOTING TARGETED INTEGRATION OF FOREIGN DNA INTO A HOST GENOME

[75] Inventors: Richard A. Katz, Elkins Park, Pa.; Anna Marie Skalka, Princeton, N.J.

[73] Assignee: Fox Chase Cancer Center, Philadelphia, Pa.

[21] Appl. No.: 08/437,317

[22] Filed: May 9, 1995

[51] Int. Cl.⁷ .......................... C07H 21/02; C07H 21/04
[52] U.S. Cl. ............................ 536/23.1; 536/24.3
[58] Field of Search .................. 536/22.1, 23.1, 536/23.2, 23.4; 436/320.1

[56] References Cited

U.S. PATENT DOCUMENTS 5,532,143   7/1996   Grosveld et al. ............... 435/69.1
5,830,707  11/1998   Bushman ....................... 435/69.7

OTHER PUBLICATIONS

Devine et al. Nucleic Acids Research 22(18): 3765–3772 (1994).
Pahl et al. Journal of Biological Chemistry 270(7): 2957–2966 (1995).
Woerner et al. Nucleic Acids Research 21(15): 3507–3511.
Bushman, PNAS 91: 9233–9237 (Sep. 1994).
Boris–Lawrie and Temin, Curr. Op. Genet. Devel. 3:102–109 (1993).
Bouck et al., Mol. Cell. Biol. 15:2663–2671 (1995).
Brent and Ptashne, Cell 43:729–736 (1985).
Burley, Curr. Op. Struct. Biol. 4:3–11 (1994).
Chow et al., Science 255:723–726 (1992).
Doolittle et al., Quart. Rev. Biol. 64:1–13 (1989).
Garfinkle, *The Retroviridae*, vol. 1, Ch. 4, pp. 107–158. J.A. Levy ed., Plenum Press, NY (1992).
Horii et al., Cell 23:689–697 (1981).
Katz and Skalka, Ann. Rev. Biochem. 63:133–173 (1994).
Katz and Skalka, Mol. Cell. Biol. 10:696–704 (1990).
Katzman et al., J. Virol. 63:5319–5327 (1989).
Kulkosky et al. Virology 206:448–456 (1995).
Latchman, *Eucaryotic Transcription Factors*, Academic Press, Inc., San Diego, CA (1991).
McNeil et al., J. Cell Biol. 98:1556–1564 (1984).
Pryciak et al., EMBO J. 11:291–303 (1992).
Terry et al., J. Virology 62:2358–2365 (1988).
Bushman and Wang, J. Virol. 68:2215–2223 (1994).
Stewart and Vogt, J. Virol. 65:6281–6231 (1991).

*Primary Examiner*—W. Gary Jones
*Assistant Examiner*—Ethan Whisenant
*Attorney, Agent, or Firm*—Dann, Dorfman, Herrell and Skillman

[57] ABSTRACT

The present invention provides novel chimeric and fusion proteins useful for facilitating site-specific integration of foreign DNA into a host genome. The chimeric enzymes of the invention comprise a DNA binding moiety fused to a retroviral integrase moiety, preferably at the precise N- or C-terminus. Nucleic acids encoding these fusion proteins can be incorporated into standard retroviral vectors, or can be provided as purified proteins. They are capable of exerting the activities of a wildtype retroviral integrase, including processing retroviral DNA termini, nicking double-stranded DNA and integrating a DNA molecule with processed retroviral termini into another DNA strand.

5 Claims, 9 Drawing Sheets

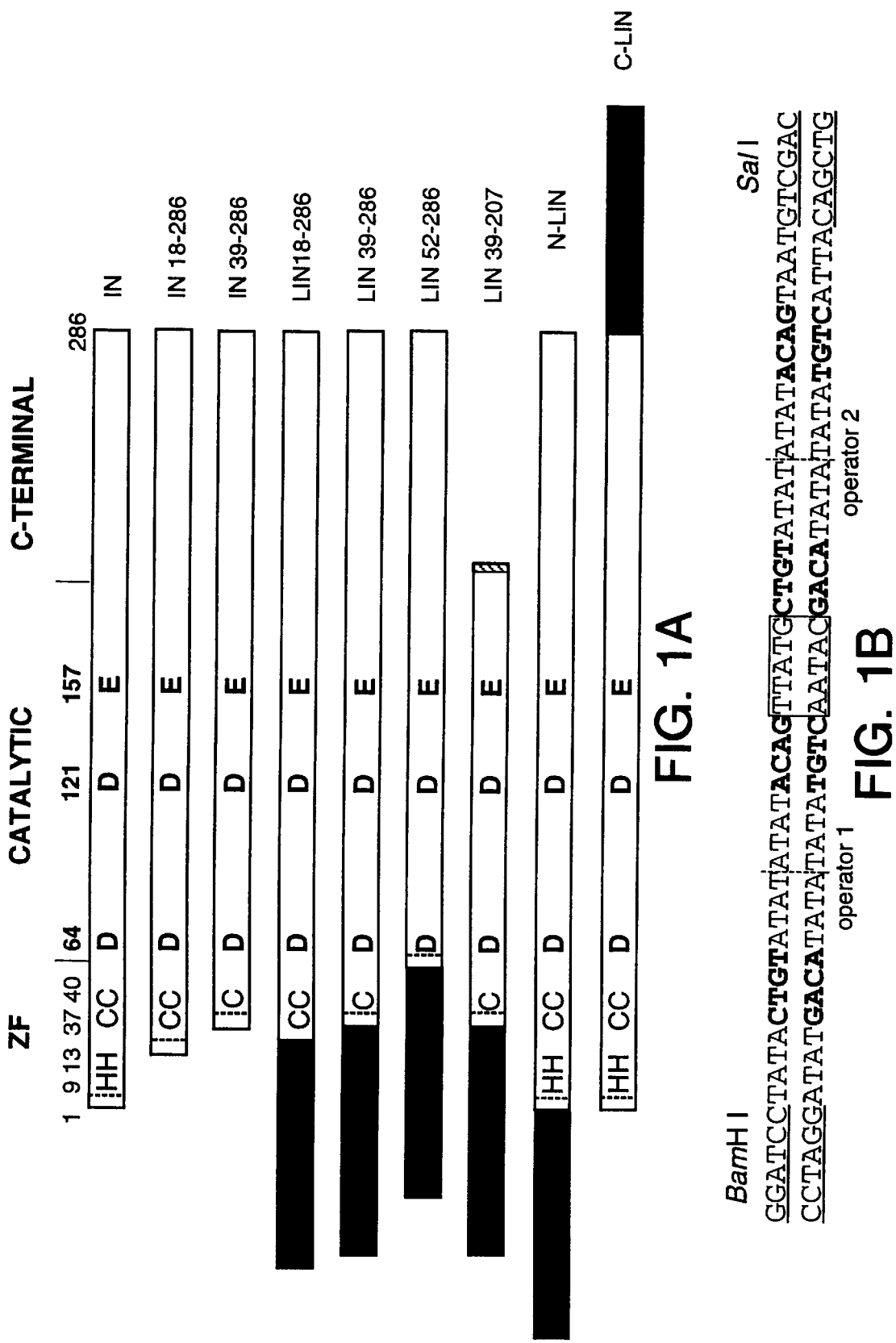

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
       (A) LENGTH: 63 base pairs
       (B) TYPE: nucleic acid
       (C) STRANDEDNESS: double
       (D) TOPOLOGY: Not Relevant (ii) MOLECULE TYPE: DNA (genomic)

(iii) HYPOTHETICAL: NO (iv) ANTI-SENSE: NO (xi) SEQUENCE DESCRIPTION: SEQ ID NO:1:

GGGGTCGACA TTACTGTATA TATATACAGC ATAACTGTAT ATATATACAG TATAGGATCC    60

GGG                                                                 63

(2) INFORMATION FOR SEQ ID NO:2:

(i) SEQUENCE CHARACTERISTICS:
       (A) LENGTH: 11 amino acids
       (B) TYPE: amino acid
       (C) STRANDEDNESS: Not Relevant
       (D) TOPOLOGY: Not Relevant (ii) MOLECULE TYPE: peptide (iii) HYPOTHETICAL: NO (iv) ANTI-SENSE: NO (xi) SEQUENCE DESCRIPTION: SEQ ID NO:2:

Ser Pro Leu Phe Ala Lys Ala Leu Thr Ala Arg
1               5                  10

(2) INFORMATION FOR SEQ ID NO:3:

(i) SEQUENCE CHARACTERISTICS:
       (A) LENGTH: 39 base pairs
       (B) TYPE: nucleic acid
       (C) STRANDEDNESS: double
       (D) TOPOLOGY: Not Relevant (ii) MOLECULE TYPE: DNA (genomic)

(iii) HYPOTHETICAL: NO (iv) ANTI-SENSE: NO (xi) SEQUENCE DESCRIPTION: SEQ ID NO:3:

CGCGCGAGCC CGTTATTCGC TAAAGCGTTA ACGGCCAGG                           39

(2) INFORMATION FOR SEQ ID NO:4:

(i) SEQUENCE CHARACTERISTICS:
       (A) LENGTH: 7 amino acids
       (B) TYPE: amino acid
       (C) STRANDEDNESS: Not Relevant
       (D) TOPOLOGY: Not Relevant (ii) MOLECULE TYPE: peptide (iii) HYPOTHETICAL: NO

```
        (iv) ANTI-SENSE: NO (xi) SEQUENCE DESCRIPTION: SEQ ID NO:4:

Val Ala Ala Gly Glu Pro Ala
1               5

(2) INFORMATION FOR SEQ ID NO:5:

(i) SEQUENCE CHARACTERISTICS:
            (A) LENGTH: 30 base pairs
            (B) TYPE: nucleic acid
            (C) STRANDEDNESS: double
            (D) TOPOLOGY: Not Relevant (ii) MOLECULE TYPE: DNA (genomic)

(iii) HYPOTHETICAL: NO (iv) ANTI-SENSE: NO (xi) SEQUENCE DESCRIPTION: SEQ ID NO:5:

GCGCGCTTAA GCTGGTTCAC CGGCAGCCAC                                        30
```

CHIMERIC ENZYME FOR PROMOTING TARGETED INTEGRATION OF FOREIGN DNA INTO A HOST GENOME

Pursuant to 35 U.S.C. §202(c), it is hereby acknowledged that the U.S. Government has certain rights in the invention described herein, which was made in part with funds from the National Institutes of Health.

FIELD OF THE INVENTION

The present invention relates to genetic modification of eucaryotic organisms. In particular, this invention provides novel fusion proteins comprising a target-specific DNA binding moiety and a retroviral integrase moiety. The enzyme is useful for facilitating target-specific integration of foreign DNA into a host genome.

BACKGROUND OF THE INVENTION

The practical utility of genetic engineering often depends on introducing inheritable genetic traits into organisms. To achieve this goal, foreign DNA must be stably integrated into the DNA of the host organism. Stable integration of foreign DNA into host DNA is often referred to as "transformation" of the host cell (or genome of the cell).

Genetic transformation in higher eucaryotes is often accomplished through the use of viral vectors which rely on stable integration in the host genome as part of their replicative cycle. Retroviruses are one of the few animal viruses that depend upon integration for replication. A number of retroviral vector systems are currently available to mediate transformation of animal genomes. Such systems utilize one or more vectors, at least one of which contains the portion of the retroviral genome responsible for integration of the viral genome into the host genome.

Integration of retroviral DNA requires a virus-encoded enzyme, the integrase (IN), which is encoded by the viral pol gene and carried within the virus particle. (For a review of the retroviral enzymes, including integrase, see Katz & Skalka, Ann. Rev. Biochem. 63: 133–173, 1994). Integration also requires cis-acting sequences at the ends of linear viral DNA. Integration is site-specific with respect to the viral DNA (it occurs at the linear ends), but appears to be nearly random with respect to host DNA.

Biochemical and genetic experiments indicate that integration takes place through two steps. First, IN nicks the viral DNA two nucelotides from the 3' ends of each DNA strand (referred to as the "processing" reaction). This nicking exposes the highly conserved CA dinucleotides, usually located two nucleotides from the 3' end of each strand. The new 3'-OH ends of each viral DNA strand are then joined to the host DNA in a second reaction (referred to as the "joining" reaction). The joining reaction is believed to proceed by a direct attack mechanism whereby the 3'-OH ends of viral DNA strands attack host DNA phosphates that are staggered by 4–6 base pairs. The simplest model for IN function is one in which a single monomer is bound to each end of viral DNA and each monomer is capable of binding viral DNA and host DNA simultaneously.

Both processing and joining activities can be assayed in vitro using short synthetic DNA substrates that mimic the single ends of retroviral DNA (see Katz & Skalka, 1994, supra). Both reactions are thought to be catalyzed by a single active site, due to the chemical similarity of the two reactions and the general inability to biochemically separate the two activities by mutagenesis.

IN is the only viral gene product required for integration of viral DNA into a host genome. For this reason, IN may be used to advantage to facilitate genetic transformation of eucaryotic cells. However, its utility is limited due to its lack of sequence specificity with respect to the host DNA. That is, IN-catalyzed integration can occur essentially at random in the genome, which could result in activation or deactivation of host genes essential for cellular function. Thus, it would be a significant advance in the art of genetic transformation to develop retroviral integrases capable of site-specifically catalyzing integration of foreign DNA into a pre-determined location in the host genome.

It is an object of the present invention to provide modified retroviral integrases capable of enhancing the integration reaction and catalyzing integration of foreign DNA at a selected target location in a host genome. It is further an object of the present invention to provide retroviral vectors that encode such modified integrases, and which also contain the foreign DNA to be inserted into the host genome.

SUMMARY OF THE INVENTION

The present invention provides novel chimeric genes and fusion proteins to enhance stable integration of foreign DNA into host DNA, and to promote site-specific integration at a selected location in a target DNA molecule. The compositions of the invention are particularly useful for enhancing integration of foreign DNA carried on retroviral vectors, which should be of wide utility as a research tool to study the organization of gene expression pathways, as well as for gene-based diagnostic and therapeutic purposes.

According to one aspect of the present invention, a chimeric enzyme is provided, which comprises a DNA binding moiety and an integrase moiety derivable from a retroelement. The enzyme is capable of binding a DNA molecule having a characteristic determinant recognized by the DNA binding moiety, and the enzyme possesses at least one activity characteristic of a retroelement integrase. Characteristic retroelement integrase activities include processing of retroelement DNA termini, nicking within double-stranded DNA, and integrating a DNA molecule having processed retroelement termini into another DNA molecule. In a preferred embodiment, the chimeric enzymes of the invention possess all three activities and integrates the processed DNA molecule into a site that neighbors the binding site recognized by the DNA binding moiety.

In preferred embodiments of the invention, the chimeric enzyme described above is constructed so that the DNA binding moiety is fused to the integrase moiety at either the amino- or carboxyl-terminus of the integrase moiety. Carboxyl-terminal fusion proteins are particularly preferred because their encoding DNAs can be incorporated into replication-competent retroviral vectors.

According to another aspect of the present invention, a nucleic acid molecule is provided, which has a sequence that encodes the chimeric enzyme described above. The nucleic acid molecule comprises a DNA binding moiety-encoding segment operably linked to an integrase-encoding segment derivable from a retroelement. The nucleic acid may be disposed within a vector, which may be a retroviral vector (either a replication competent vector or a "helper" virus), a cloning vector or an expression vector. In a preferred embodiment, the nucleic acid is disposed within a retroviral vector. If the nucleic acid encodes a chimeric enzyme in which the DNA binding moiety is fused to the C-terminus of the integrase moiety, a retroviral vector may be constructed. These retroviral vectors may also contain a foreign DNA to be inserted into a host genome.

The novel chimeric genes and fusion proteins of the present invention represent a significant advance in the art of stable integration of foreign genes into host genomes. Whereas current retroviral integrase systems are capable only of catalyzing random integration of foreign DNA at low efficiency, the modified integrases of the invention are capable of enhancing the integration reaction and catalyzing integration of foreign DNA at selected targets located in a host genome.

BRIEF DESCRIPTION OF THE DRAWINGS

FIGS. 1A and 1B: FIG. 1A shows a schematic representation of avian sarcoma virus (ASV) IN protein and various derivatives. The wild type IN protein, 286 amino acids in length, is depicted. The highly conserved amino acid residues are represented with the single letter code. Their position numbers and the domains that they define are also indicated. The putative catalytic residues are in bold. The filled boxes indicate the LexA repressor DNA binding domain (87 amino acids). The numbering of the various derivatives reflects the amino acids that are retained. The dashed vertical lines indicate the first four amino acids of IN that are retained as a "leader" or "spacer" in the majority of deletion and fusion proteins. The hatched region in LIN 39-207 indicates the presence of two heterologous amino acids at the C-terminus. FIG. 1B shows the lexA operator sequence (Sequence I.D. No. 1) used as a target for experiments shown in FIGS. 3 and 4. Restriction sites for cloning into pBR322 are shown. The operator core sequences are shown in bold. The vertical lines indicate axis of dyad symmetry for each operator. Boxed region indicates the spacer between the two operators.

FIG. 2 (FIGS. 2A and 2B). In vitro processing assay for IN and IN derivatives.

FIG. 5 (FIGS. 5A, 5B and 5C). Nicking (double strand break) assay for ASV IN and derivatives. Supercoiled substrate (form I, FI) was used in FIGS. 5A and 5B. Linear substrate was used in FIG. 5C. Proteins used for reactions are indicated above lanes. FIG. 5A: plasmid (pNDE-1), a pBR322 derivative lacking lexA operators was used as a substrate. DNA forms (F) I, II and III are indicated. Marker DNA sizes are indicated in base pairs. Lane 1, marked CON, indicates that the reaction was incubated in the absence of IN. FIG. 5B: The plasmid (pBRBSLexAOP) was used as a substrate. This plasmid contains several tandem lexA operators. The F II band in the starting material (CON, Lane 1) may also contain supercoil dimer and a double strand break would produce a linear dimer [denoted F III (D?)]

FIG. 7 (FIGS. 7A and 7B). Virus replication as measured by the reverse transcriptase assay after DNA transfection and infection of CEFS.

DETAILED DESCRIPTION OF THE INVENTION

Figure 2A:
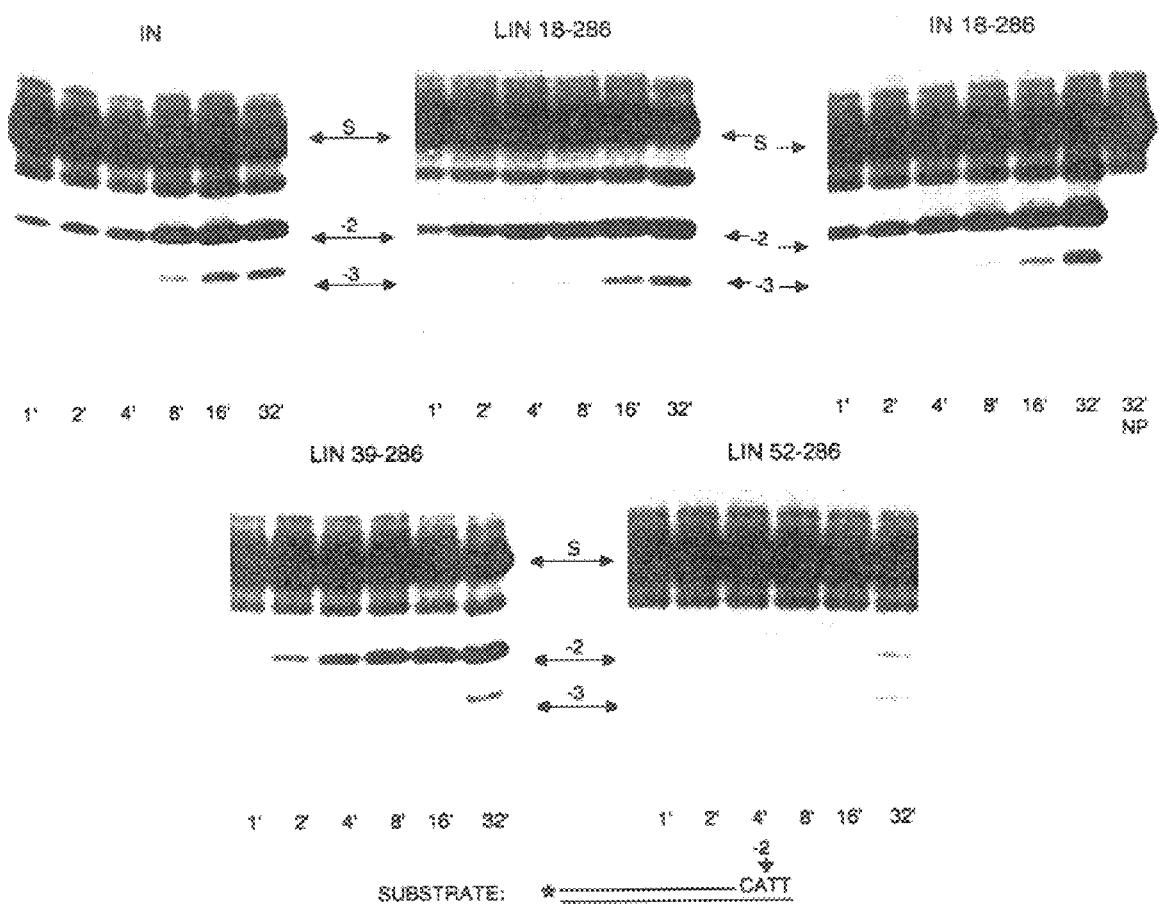
FIG. 2A: wildtype IN, IN 18-286, L-IN 39-286, L-IN 52-286.

It has been discovered in accordance with the present invention that the retroviral integrase (IN) can be fused with a heterologous DNA binding moiety (DB) to form a chimeric enzyme capable of enhancing integration efficiency and facilitating site-specific integration of a foreign DNA molecule into a target DNA. These chimeric enzymes can be constructed as precise fusions of a DB to the N-terminus or C-terminus of retroviral IN. Alternatively, chimeric enzymes of the invention can be constructed by deleting a portion of the N-terminus of IN (specifically the ZF region, which in ASV is up to approximately 40 amino acids from the N-terminus) and thereafter fusing the DB to the N-terminal truncated IN.

As described in the background section, wildtype IN is capable of catalyzing all reactions necessary for integration of retroviral DNA. The precise C- and N-terminal fusion proteins of the present invention retain all activities ascribable to native IN, and are additionally capable of targeting a foreign gene to the target sequence recognized by the DNA binding moiety of the fusion protein and thereafter promoting the enhanced use of integration sites nearby the target DNA sequence. When optimized, these proteins may also enhance efficiency of the integration reaction, as well as facilitate targeted integration. Additionally, it has been discovered in accordance with the present invention that a retrovirus engineered to encode a chimeric enzyme comprising a C-terminal fusion of IN and a DNA binding moiety is competent to replicate within host cells.

N-terminal fusions of the DNA binding moiety to a location within the integrase ZF region are also capable of exerting most of the activities of native IN (i.e. processing viral DNA termini, concerted nicking of target DNA and joining of viral DNA to target DNA); however, integration catalyzed by these chimeric enzymes is not targeted to a neighboring site, as it is in the precise N- and C-terminal fusion proteins. These chimeric enzymes should find an additional utility as site-specific DNA cleaving agents, due to their retention of the integrase concerted nicking activity in the vicinity of the DNA binding site.

The chimeric enzymes of the present invention are useful in a variety of forms for the purpose of facilitating stable integration of foreign DNA at a selected target position in a host chromosome or genome. In one embodiment, currently-available retroviral vectors can be modified such that they encode a DB/IN chimeric enzyme (instead of a native integrase). Such vectors may also encode the foreign DNA desired for insertion into a host genome, or they may be utilized as retroviral helper vectors to integrate foreign DNA provided on a separate gene transfer vehicle. Alternatively, purified enzymes of the invention may be provided as adjuvant with a foreign DNA of interest, to enhance targeted integration of the DNA. The chimeric enzymes of the invention are useful as research tools for studying the effect of insertional activation or disruption of genes in cultured cells or in animal model systems. More importantly, the chimeric enzymes of the invention can be used as diagnostic/therapeutic agents in a variety of currently available and developing gene transfer methodologies.

The detailed description set forth below describes preferred methods for making and using the chimeric enzymes of the present invention. Any molecular cloning or gene transfer techniques not specifically described are carried out by standard methods, for example as generally set forth in Sambrook et al., "DNA Cloning, A Laboratory Manual," Cold Spring Harbor Laboratories, 1989 (hereinafter Sambrook et al.); and Ausubel et al. (Editors), "Current Protocols in Molecular Biology," John Wiley & Sons, Inc., 1995 (hereinafter Ausubel et al.).

I. PREPARATION OF CHIMERIC ENZYMES COMPRISING A DNA BINDING MOIETY AND AN INTEGRASE MOIETY

The chimeric enzymes of the present invention comprise two components: an integrase (IN) domain and a DNA binding (DB) domain. These domains may be arranged as precise C- or N-terminal fusions with respect to the integrase moiety, or may comprise N-terminal fusions wherein a portion of the IN N-terminus has first been deleted. In accordance with the present invention, it has been discovered that the ZF domain of IN (comprising approximately the first 40 amino acids of the protein in ASV) is not essential to maintain the activities of the IN moiety. The fusion proteins of the invention are sometimes referred to herein as "DB/IN" or as "N-DB/IN" or "C-DB/IN" to denote that the DNA binding moiety is attached at the N-terminus or the C-terminus of the IN moiety, respectively. Finally, chimeric enzymes that comprise an N-terminal fusion in which a portion of the IN moiety has been deleted are sometimes referred to herein as "DB/IN" followed by a pair of numbers, which refer to the amino acid residues included in the IN moiety of the fusion protein (for example, residues 18–286 of ASV IN fused to the LexA DNA binding domain, as described in Example 1, is referred to as LIN 18-286).

The DB/IN fusion proteins of the invention are prepared by recombinant DNA methods, in which DNA sequences encoding each domain are "operably linked" together such that upon expression, a fusion protein having the targeting and integrase functions described above is produced. As used herein, the term "operably linked" means that the DNA segments encoding the fusion protein are assembled with respect to each other, and with respect to an expression vector in which they are inserted (including retroviral vectors), in such a manner that a functional fusion protein is effectively expressed. The selection of appropriate promoters and other 5' and 3' regulatory regions, as well as the assembly of DNA segments to form an open reading frame, employs standard methodology well known to those skilled in the art.

Thus, preparing the chimeric enzymes of the invention involves selecting DNA sequences encoding each of the aforementioned components, operably linking the respective sequences together in an appropriate vector, and expressing the sequences to produce the chimeric enzyme. Each of these steps is described below.

It will be appreciated by persons skilled in the art that the DNA components assembled for expressing the chimeric enzymes of the present invention can be prepared in a variety of ways, including DNA synthesis, cloning, mutagenesis, amplification, enzymatic digestion, and similar methods, all available in the standard literature. Additionally, certain of the components can be obtained easily through commercial sources or by access to public repositories, such as the American Type Culture Collection. Alternatively, components that are not readily available, and/or for which sequence information is not available, can be isolated from biological sources using standard hybridization methods and homologous probes that are available.

Due to the high level of conservation among retroviruses, retrotransposons and other retroelements, DNA sequences encoding the integrase moiety of the fusion proteins of the invention can be selected from any of these sources. As used herein, the term "retrovirus" refers to a class of viruses in which the genetic material is RNA, but which completes its replicative cycle by means of a DNA intermediate, which becomes integrated into the genomic DNA of host cells (see Background section). The term "retrotransposon" refers to a class of mobile DNA elements that possess long terminal repeats (LTRs, generally a few hundred base pairs in length), which replicate through RNA intermediates that are copied by reverse transcriptase (a retrotransposon may be thought of as a retrovirus for which an infectious extracellular form does not exist, or has not yet been discovered). The term "retroelement" refers collectively to retroviral DNA, retrotransposons and other transposable elements having the above-described characteristics. Retroelements encode at least one, and generally all, of the following three enzymes: reverse transcriptase (RT), protease (PR) and integrase (IN). Any retroelement that encodes an integrase may be utilized as a source for DNA sequences encoding the IN moiety of the invention. Such retroelements include, but are not limited to: (1) retroviruses such as human T-cell leukemia virus (HTLV) types I and II, bovine leukemia virus (BLV), simian retrovirus type I (SRV-I), mouse mammary tumor virus (MMTV), avian sarcoma virus (ASV), human immunodeficiency virus (HIV), human spuma (foamy) virus (HFV), visna lentivirus (VISNA), Moloney mouse leukemia virus (Mo-MLV), feline immunodeficiency virus (FIV) caprine arthritis-encephalitis virus (CAEV) equine infectious anemia virus (EIAV), human endogenous retrovirus (HERV) type C and type K, and hamster intercisternal particle (IAP-18); and (2) retrotransposons and other retroelements, such as Ty-1, Ty-3, Copia, Gypsy, 297, 17.6, and 412. For a review of eucaryotic and procaryotic retroelements, see, e.g., Doolittle et al., Quarterly Review of Biology 64: 1–30 (1989); Garfinkle Chapter 4 in *The Retroviridae*, Volume 1, J. A. Levy, Ed., Plenum Press, New York (1992) pages 107–158.

A variety of DNA binding proteins have been isolated and characterized in recent years. Any of these DNA binding proteins can serve as appropriate sources for the DNA binding moiety of DB/IN fusion proteins. Moreover, as new DNA binding proteins are isolated and characterized, these may also be utilized to construct DB/IN proteins of the invention. For optimum practice of the present invention, it is important to select DNA binding domains that recognize one or more specific characteristic determinants of a DNA molecule, rather than binding randomly to DNA. As used herein, the term "characteristic determinant" refers to one or more sequence or structural features unique to a particular gene or other specified location on a DNA molecule. As will be appreciated by those skilled in the art, such characteristic determinants generally involve a specific primary DNA sequence, as well as positioning of one or more such sequences relative to one another on a DNA double-helix, possibly combined with other structural features of eucaryotic chromosomal DNA.

Chimeric enzymes comprising the LexA DNA binding domain are described in detail in Example 1. These fusion proteins serve to demonstrate that integrase indeed can be constructed as a fusion protein with a DNA binding moiety to produce a chimeric enzyme that can facilitate site-specific integration of a foreign gene. However, the greater practical utility of the invention is directed to eucaryotic host DNA since retroviral vectors are used in eurcaryotic systems. Accordingly, DNA binding proteins targeted to eucaryotic genes are preferred for practice of the invention. Particularly preferred are eucaryotic transcription factors that possess DNA binding domains, such as those that act in concert with RNA polymerase, as described by Burley, Current Opinion in Structural Biology 4: 3–11 (1994). These include, but are not limited to: TATA box binding proteins (TBP), specifically TBP isoform 2; b/hlh/z factors, such as Max and USF; helix-turn-helix variants, such as the third repeat of c-Myb, the POU-specific domain Oct-1, the homeodomain from LSB1/HNF1 and the fork head domain of HNF-3γ; the DNA binding domain of GATA-1; the nucleic acid binding domain of transcription factor IIS;and the 5 zinc-finger GLI DNA binding domain. Also particularly preferred are eucaryotic transcription factors such those that regulate differential gene expression in cellular growth, development and differentiation (see, e.g., D. S. Latchman, "Eukaryotic Transcription Factors," Academic Press, Inc., San Diego, 1991). These include, but are not limited to, NFκB, KBF1 C/EBP and CRE binding proteins, and other transcription regulators encoded by genes such as erbA, ets, fos, jun, myb, myc, rel and spi-1.

As discussed above, DB/IN enzymes of the invention may be utilized as purified proteins or as DNA sequences encoding the protein, to be included on a retroviral vector and expressed in situ by cellular enzymes. Thus, either retroviral vectors or expression vector systems will be required to practice the invention.

Numerous retroviral vector systems are publicly or commercially available. These systems generally comprise vectors for carrying the foreign DNA of interest and a packaging or helper cell line which contains viral sequences encoding trans-acting proteins (although some vectors comprise all sequences necessary for replication competence). Several recently-developed retroviral vector systems are described by Boris-Lawrie & Temin, Curr. Op. Genet. Devel. 3: 102–109 (1993). Other are known in the art (see, e.g., Ausubel et al., Chapter 9.10, 9.11).

Retroviral vectors can be modified to substitute a DB/IN of the invention for the standard integrase gene carried on the vector, utilizing standard recombinant DNA techniques. Alternatively, the integrase gene carried on a retroviral vector may be modified by adding sequences encoding a DNA binding moiety at the N- or C-terminus, or within the N-terminal ZF domain, in accordance with the description set forth above. These substitutions or modifications may be carried out on retroviral vectors destined to contain the foreign DNA of interest or, alternatively, on "helper" retroviral vectors in a gene transfer system in which the foreign DNA of interest is carried on a separate vector. Modification of a retroviral vector to comprise a DB/IN-encoding gene of the invention is described in greater detail in Example 1.

Retroviral vectors comprising DB/IN sequences are used according to standard methods to transfect eucaryotic cells (either cultured cells or cells within a living organism). The chimeric enzyme of the invention is then expressed within the transfected cells and is thus available to facilitate targeted integration of foreign genes carried on that same vector or a separate vector.

The chimeric enzymes of the invention may also be produced using other in vitro expression methods known in the art. For example, DNA sequences encoding the protein may be cloned into an appropriate in vitro transcription vector, such as pSP64 or pSP65, for in vitro transcription, followed by cell-free translation in a suitable cell-free translation system, such as wheat germ or rabbit reticulocytes. In vitro transcription and translation systems are commercially available, e.g., from Promega Biotech, Madison, Wis. or BRL, Rockville, Md.

Alternatively, according to a preferred embodiment, the chimeric enzymes may be produced by expression in a suitable procaryotic or eucaryotic cellular system. For example, DB/IN sequences may be inserted into a plasmid vector adapted for expression in a bacterial cell, such as *E. coli*, or into a baculovirus vector for expression in an insect cell. Such vectors comprise the regulatory elements necessary for expression of the DNA in the bacterial or eucaryotic host cell, positioned in such a manner as to permit expression of the DNA in the host cell. Production of a chimeric enzyme of the invention by expression in a procaryotic system is described in greater detail in Example 1.

The protein produced by expression in a recombinant procaryotic or a eucaryotic system may be purified according to methods known in the art. In a preferred embodiment, a commercially available expression/secretion system can be used, whereby the recombinant protein is expressed and thereafter secreted from the host cell, to be easily purified from the surrounding medium. If expression/secretion vectors are not used, an alternative approach involves purifying the recombinant protein by affinity separation, such as by immunological interaction with antibodies that bind specifically to one or more moieties of the recombinant protein. Such methods are commonly used by skilled practitioners. Purification of a chimeric enzyme of the invention after expression in a procaryotic system is described in greater detail in Example 1.

II. METHODS OF USING DB/IN ENZYMES, AND SPECIFIC APPLICATIONS

The methods of the invention generally involve combining host DNA (e.g., genomic DNA from higher eucaryotes) with foreign DNA in the presence of a chimeric enzyme of the invention in such a manner as to enable the enzyme to catalyze the site-specific integration of the foreign DNA into a selected target site of the host DNA. The foreign DNA is carried within a retroviral vector, or is modified to provide linear double-stranded segments that have terminal DNA sequences recognizable by the DB/IN enzyme. The enzyme thereafter supplies the necessary processing and joining catalytic functions for integration into the pre-determined target site, and cellular repair enzymes (e.g., DNA polymerases and ligases) provide the requisite gap-filling and ligation functions to accomplish full integration.

The chimeric enzymes of the invention can be utilized for site-specific modification of host DNA either extracellularly or intracellularly. In the extracellular application, host DNA is removed from cells or otherwise purified, either as a total DNA fraction or as intact chromosomes, and combined with the foreign DNA of interest and the chimeric enzymes (or gene encoding the enzyme) in a suitable biological buffer, along with any other biological reagents necessary for completing integration of the foreign DNA into the host DNA. This in vitro utility of the chimeric enzymes of the invention should find broad application in preliminary research, in which the effect of targeted, stable insertion of a foreign DNA into a host gene or chromosome is being studied or explored.

In most applications of the invention, it is preferable to utilize the DB/IN chimeric enzymes in situ, i.e., within cells containing host DNA. To accomplish this, the chimeric enzyme is introduced into cells by expression from a retrovirus helper or vector, or as protein or DNA. For a retroviral helper, a cell line is created that expresses all retroviral proteins, with the DB/IN replacing the native integrase. The retroviral vector is then introduced by transfection into a cell of interest. Similarly, a replication-competent vector comprising C-terminal DB/IN fusions and the foreign DNA of interest, may be introduced into a cell line by transfection or by a variety of other methods known in the art for introducing DNA and/or proteins into a cell. Such methods include, but are not limited to: (1) calcium phosphate co-precipitation; (2) DEAE-dextran treatment; (3) electroporation; (4) biolistic delivery (i.e., bombardment of cells or tissues with DNA-coated microparticles); (5) microinjection; (6) "scrape-loading," as described by McNeil et al., J. Cell Biol. 98: 1556–1564 (1984); and (7) liposome- or erythrocyte-mediated transfection. These and other currently-available methods may be utilized on cultured or non-cultured cells, excised tissues or within a living organism.

The chimeric enzymes of the present invention will find their broadest utility as general enhancers of the integration reaction and as facilitators of targeted integration of foreign DNA into host DNA within cultured cells or within cells of a living organism. The enzymes will be useful as a research tool to study the effect of insertional disruption or enhancement of one or more genes within the natural cellular environment. As a specific example, transcription factors, which are the subjects of intensive research, are known to regulate groups of genes at different stages of development or at different times in a cell cycle. These genes are "turned on" or "turned off" at specific developmental stages or times, such regulation orchestrating the expression of genes under control of the transcription factors. It is now known that these factors are open for activation by certain changes occurring in the chromosomal DNA which enable binding of DNA binding proteins that activate expression of the transcription factors. Since several of these DNA binding proteins have already been isolated and characterized, their DNA binding domains can be utilized in construction of DB/IN proteins of the invention. Because the protein is directed to a binding domain which is only "open" at certain times, the chimeric enzyme may be used as a probe to explore when, or at which developmental stages, a particular transcription factor is open for activation.

As another specific example, the DB/IN chimeric enzymes will be useful as a diagnostic and/or therapeutic tool, e.g., for disrupting genes known to have a detrimental effect. For instance, certain regulatory proteins are involved in cellular proliferation. For such proteins in which an activating DNA binding protein is known and has been characterized (for a list of examples, see Latchman, 1991, supra, at page 155), chimeric enzymes can be produced in accordance with the present invention to specifically disrupt expression of such genes by stable integration of a foreign DNA at the binding locus, thereby permanently inactivating the detrimental gene. In comparison, many gene- or RNA-inactivating strategies involve only transient measures, such as introduction of antisense molecules or ribozymes, and do not permanently inactivate a gene. In addition, as it becomes feasible to design DNA binding domains that bind to selected DNA recognition sequences or other characteristic determinants, DB/IN enzymes may be constructed that catalyze integration into a specific target site (e.g., at innocuous sites between expressed genes), to enable gene addition therapy without disrupting normal gene expression.

The use of the chimeric enzymes of the invention to disrupt or augment gene expression can first be explored in cultured cells, and thereafter can be utilized in living organisms. In this regard, the chimeric enzymes of the invention can be used to particular advantage for gene transfer in germline cells, such as bone marrow or stem cells from peripheral blood. These cells can be genetically manipulated ex vivo during the course of a normal autologous stem cell transplantation procedure.

The DB/IN enzymes of the present invention should be of substantial utility in facilitating site specific integration of foreign DNA molecules into host DNA in vitro, in cultured cells, and in living animals. This is a significant advance in the art with respect to stable transformation of eucaryotic DNA by way of retroviral vectors, which heretofore were capable only of catalyzing random integration events.

The following example is provided to describe the invention in further detail. This example is intended to illustrate and not to limit the invention.

EXAMPLE 1

In this example, we describe in detail chimeric IN proteins containing the lexA DNA binding domain (DBD) fused precisely at the N- or C-termini of ASV IN, or within the N-terminal ZF domain of ASV IN. These fusion proteins demonstrate great potential for enhancing targeted retroviral integration into host DNA.

MATERIALS AND METHODS

Construction and purification of LexA-IN fusion proteins. We constructed a set of six LexA-ASV IN fusions in which the LexA DBD replaced various portions of the N-terminus of IN or was fused directly to the N- or C-termini (FIG. 1). The sequence encoding the LexA DNA binding domain was derived from the plasmid pRB451, kindly provided by R. Brent (the sequence is also publicly available from the GENEBANK-National Center for Biotechnology Information, Accession No. J01643-V00299-V00300; see also Horii et al., Cell 23: 689–697 1981). PCR primers were designed to amplify the region corresponding to the LexA DBD, codons 1–87. For N-LIN, EcoRI sites were engineered into both PCR primers such that the LexA DBD coding region could be inserted into the unique EcoRI site located at the 5'-end of the RSV IN reading frame in the expression vector pRC23IN (pRC23 is a commercially available expression vector; pRC23IN is described as "pRC23-p32" by Terry et al., J. Virol. 62: 2358–2365, 1988). N-terminal deletion mutations in which residues 5–52 or 5–39 of RSV IN have been deleted were described elsewhere (Kulkosky et al., Virology 206: 448–456, 1995). These N-terminal deletions were assembled into pRC23IN. In the deletion constructs, the EcoRI site at the 5'-end of IN has been retained along with codons for the first four IN amino acids. The LexA DBD sequence, adapted with EcoRI site, was inserted at the unique EcoRI site in these two constructs, producing the construct LIN 39-286 and LIN 52-286 (FIG. 1). A similar approach was used to construct LIN 39-207 from 39-207, which was described elsewhere (Kulkosky et al., 1995, supra).

The LIN 18-286 was constructed using a different strategy. The C-terminal border of the LexA DBD sequence is defined by an XmnI site, so an XmnI partial digest was performed on pRB451. The PstI site in the amp gene is common to pRC23IN and pRB451 and this was used to transfer a small cassette containing the Tac promoter from pRB451 along with the first 87 amino acids up to the XmnI site. This fragment was cloned into pRC23IN that had been cleaved with BssHII, repaired and cleaved with PstI. The BssHII site corresponds to codon 17 of IN. Ligation of the blunt XmnI site to the repaired BssHII site resulted in an in-frame fusion between the LexA DBD codon 87 and ASV IN codon 18. An analogous deletion (IN 18-286), missing IN codons 5–17, was constructed by cleaving pRC23IN with BssHII and EcoRI and inserting a small EcoRI/BssHII linker that reestablished only the first four codons.

The C-LIN (FIGS. 1 and 6) was constructed in a manner that was amenable for reassembly into the viral genome. The LexA DBD coding region was amplified from the plasmid pRB451. The PCR primers included a BanII site on the upstream side and an AflII site on the downstream side. The downstream PCR primer contained a stop codon which would terminate the LexA DBD after amino acid residue 87. The BanII/AflII-adapted LexA DBD fragment was inserted into pSP73ASV-IS1 (Bouck et al., Molec. Cell. Biol. 15: 2663–2671, 1995) which contains the C-terminus of integrase as well as an adapter that separates the IN coding region from the overlapping env reading frame. The adapter also contains a single nucleotide change that was selected in vivo, which restores regulated splicing at the neighboring env splice site.

The proteins diagrammed in FIG. 1 were purified from E.coli as described previously (Kulkosky et al., 1995, supra), except for LIN 18-286, which was purified by an earlier method (Terry et al., 1988, supra). All proteins were soluble and behaved similarly to the wildtype ASV IN.

LexA operator DNA. For the DNA nicking experiments shown in FIG. 5, a consensus lexA operator segment was present which was in a ca. 750 bp BamHI/SalI fragment from the plasmid 1107 kindly provided by R. Brent, (Brent & Ptashne, Cell 43: 729–736, 1985). The operator region was transferred to pBR322 by replacing the BamHI/SalI fragment. This plasmid is denoted pBRBSLexAOP. The lexA operator had XhoI ends and was inserted into an XhoI site. When partial digests were carried out to confirm the presence of the 24 bp operator, we noted a ladder of five bands, consistent with the presence of four tandem operators. Sequence analysis confirmed the presence of multiple operators.

A second plasmid was constructed containing two tandem lexA operators. A synthetic 63mer oligonucleotide duplex was prepared containing: BamHI and SalI restriction site for cloning into pBR322, two consensus operators with upstream and downstream spacers and a spacer sequence between the two operators derived from the natural lexA tandem operators (FIG. 1). The resulting plasmid pBR711-2 was sequenced to confirm the presence of the operator segment.

Processing assay. LexA-IN fusions were assayed for the ability to process viral DNA ends using a model substrate described by Katzman et al., J. Virol. 63: 5319–5327 (1989). Briefly, the substrate consists of a synthetic duplex of 18 bp analogous to an end of linear viral DNA. Incubation with IN in the presence of 3 mM $MnCl_2$ results in specific nicking two nucleotides from the 3' end of one strand ("processing"). This reaction removes the TT dinucleotide to produce a recessed end and exposes the highly conserved CA dinucleotide, which becomes joined to the host DNA. The 5'-end of the target strand is labeled and the product, which is two nucleotides shorter, is detected by electrophoresis on a denaturing gel.

Plasmid nicking assay. Assays for concerted nicking were carried out as described by Terry et al., 1988, supra, with some modifications. The reaction mix contained 20 mM Tris-HCl pH 7.4, 3 mM $MnCl_2$, 100 ngs of supercoiled plasmid DNA or linear DNA, and 5 pmoles of IN or lexA-IN protein. Reactions were incubated for 0.5 to 2 hours and were loaded on a 1% agarose gel. We observed that de-proteinization did not affect the results, so this step was not included. The gels were stained with ethidium bromide and visualized under ultraviolet light.

Assay for integration into pBR322 targets containing lexA operators. Integration of the model viral DNA duplex into a heterologous target was measured using a PCR-based assay similar to that described by Pryciak et al., EMBO J. 11: 291–303 (1992). The target DNAs, pBR322 derivatives, contain the lexA operator region. To measure integration into a specific region, a "target" PCR primer was selected, which was ca. 250 bp from the lexA operator region. The "viral" primer was identical to the 16nt DNA strand to be joined to the target DNA. The length of the PCR product corresponds to the distance from the target primer site to the integration site. Integration assays contained approximately 0.2 pmoles of PstI linerarized plasmid target DNA, 35 pmoles of IN or IN-lexA fusion protein and 0.1 pmol of viral DNA ends (model substrate). The reaction mixture contained 20 mM Tris-HCl and 5 mM $MgCl_2$. The viral DNA substrate was a 18 mer/16 mer duplex with a recessed end. This corresponds to a processed viral DNA end, as described previously (Katzman et al., 1989, supra). The viral DNA substrate and IN were incubated on ice for 10 minutes and the targeted DNA and metal were then added. Reactions were carried out for 60 to 90 minutes at 37° C. The reaction mix was treated with Proteinase K (200 μg/ml f.c.) and 0.5% SDS for one hour at 37° C. Carrier tRNA was added and nucleic acids were purified by phenol extraction and concentrated by ethanol precipitation. The target DNA, now containing inserted viral DNA ends, was resuspended in 100 μl 200 mM Tris-HCl (pH 7), 1 mM EDTA. Recovery of target DNA was monitored by agarose gel electrophoresis. Samples (5 to 10 μl) were removed for PCR analysis. Standard PCR conditions were 1 minute at 94° C., 1 minute at 37° C. and 1 minute at 72° C., 30 cycles. The target PCR primer was $^{32}$P end-labelled and viral PCR primer was unlabelled. Products were analyzed on 7% acrylamide-urea sequencing gels. Fragment sizes were determined using a ØX174HaeIII digest and a 10 bp ladder (Bethesda Research Labs).

Transfections, virus replication assays and western blot analysis. Transfections of chicken embryo fibroblasts was carried out as described by Katz & Skalka, Mol. Cell Biol. 10: 696–704 (1990), using the DEAE-dextran method. Virus production was monitored using a standard reverse transcriptase assay. For protein analysis, virus particles were pelleted from 10 ml of culture supernatant and proteins were fractionated on SDS polyacrylamide gels. Western blots were carried out as described previously using rabbit polyclonal antibody directed against the LexA repressor protein and rabbit polyclonal antibody directed against bacterially-produced ASV IN ("p36") (Stewart & Vogt, J. Virol. 65: 6218–6231, 1991).

RESULTS

Construction of lexA repressor DBD-IN fusions proteins. The lexA repressor is composed of a DNA binding domain (DBD, residues 1–87) and a dimerization domain (residues 88–202). High affinity binding of the repressor to cognate operators requires dimerization. We designed several truncated and full length ASV IN proteins containing the LexA repressor DBD (FIG. 1). Our initial premise was that the N- and C- termini of IN may be involved in recognition of host or viral DNA, and by replacing either terminus, we could determine whether a heterologous DNA binding domain could complement IN function. The isolated central domain of ASV IN retains a nonspecific endonuclease and a cleavage-ligation activity; therefore this domain must be capable of DNA binding independently of the N- and C-termini. The central domain of IN also contributes to dimerization and therefore could provide the dimerization function required for high affinity binding of the lexA DBD. We fused the lexA DBD to the N-terminus of ASV IN at residues 18, 39 and 52, which resulted in partial or complete removal of the ZF domain. In addition, we designed several analogous IN deletions which lacked the lexA DBD. The lexA DBD was also fused to the central domain, 39-207. Lastly we constructed two fusions in which the LexA DBD was present at either the N- or C-terminus (n-LIN and C-LIN, respectively). All of the fusions shown in FIG. 1 were soluble when expressed in E. coli. Two additional constructs were designed to produce protein in which the LexA DNA binding domain was either tethered at the N-terminus through a spacer or fused near the C-terminus (not shown). Proteins produced from these clones could not be purified by standard methods and were not analyzed further (not shown).

Figure 2B:
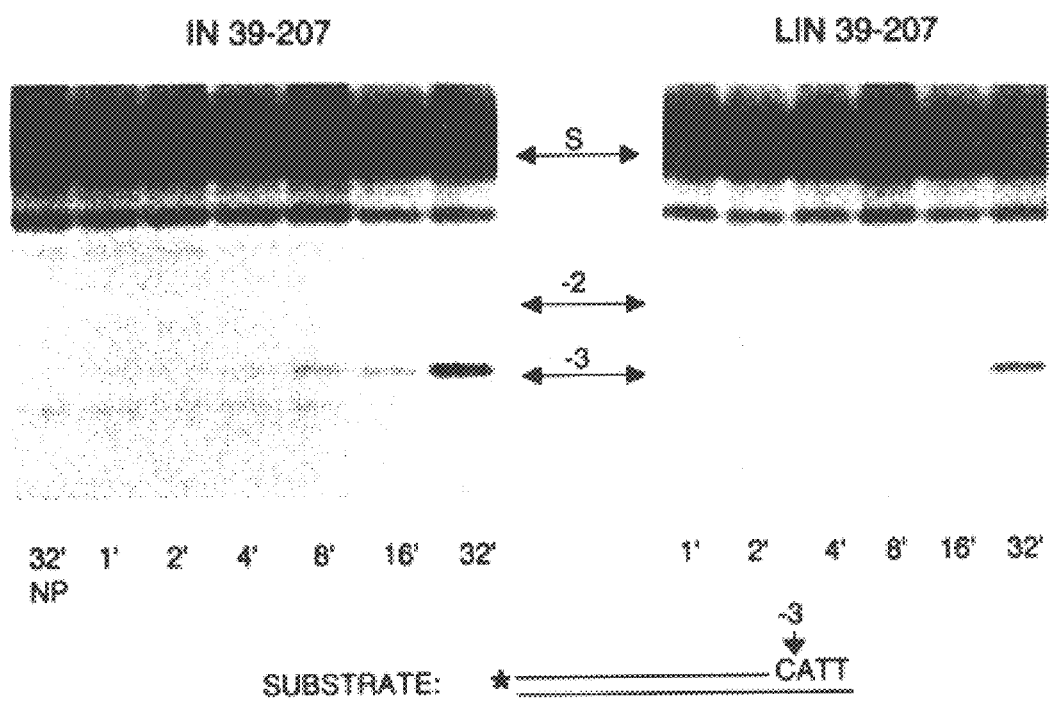
FIG. 2B: IN 39-207, L-IN 39-207. Time course in indicated, NP indicates a control incubation without protein. Reaction products were fractionated on polyacrylamide-urea sequencing gels. "S" indicates labeled substrate strand from the duplex substrate that mimics the retroviral DNA end (see diagrams in lower parts of the figures, asterisk indicates $^{32}$P label). ASV IN nicks the substrate between the A and T (as indicated by arrow in diagram FIG. 2A), releasing the TT dinucleotide. This produces a strand two nucleotides shorter than the substrate (denote "−2" band). The "−3" nicking (FIG. 2B) represents a non-specific activity which is prominent when using the preferred $Mn^{++}$ ion as a co-factor; the catalytic domain fragment retains this "−3" activity.

Processing and endonuclease activities of fusion proteins. The chimeric proteins and deletion mutants shown in FIG. 1 were assayed for processing activity in vitro using standard model substrates (FIG. 2). Wild type ASV IN is able to cleave the DNA specifically following the conserved CA dinucleotide as indicated. Fusion of the LexA DBD to IN amino acid positions 18 or 39 resulted in retention of wildtype processing activity (IN 18-286, IN 39-286). Joining activity, manifested by insertion of the newly formed ends in other substrate molecules, could also be detected on longer exposures of the gel (data not shown) and was similar to wildtype. Similar activities were noted with constructs IN 18-286 and IN 39-286, indicating that activity did not depend on the presence of the LexA DBD (data not shown for the IN 39-286 protein). Fusion of the LexA DBD at residue 52 (LIN 52-286), however, resulted in a dramatic reduction of processing activity. The non-fused version of 52-286 appeared to be unstable in E. coil and thus could not be assayed.

We previously observed that deletion of the C-terminus of IN (IN 1-207 construct) resulted in loss of processing activity, but retention of a Mn$^{++}$-dependent endonuclease activity which cleaves between the C and A ("–3" cut), as well as other sites (Kulkosky et al., 1995, supra). The wildtype ASV IN also displayed the "–3" cutting activity (FIG. 2). This activity is a property of ASV IN, as indicated by specific inhibition by certain anti-ASV IN monoclonal antibodies. The IN 39-207 and IN 52-207 fragments retained this "–3" cutting activity (FIG. 2, data not shown for IN 52-207). The central domain fragments also retained a cleavage-ligation activity, similar to the "disintegration" activity originally described by Chow et al., Science 255: 723–726 (1992). Fusion of the lexA DBD to the 39-207 fragment resulted in retention of this "–3" cleavage activity. From the results in FIG. 2, we concluded that the N-terminal ZF-domain (1-40) is not essential for processing activity as assayed under these conditions. Lastly, the N-LIN and C-LIN proteins were assayed for processing and joining and displayed processing and joining activities similar to wild type IN (data not shown).

The LexA DBD can influence integration site selection. Retroviral DNA integration into the host cell DNA is essentially random. Some models for IN structure-function suggest that a "non-specific DNA-binding activity" could account for random selection of host integration sites. To determine whether the presence of a specific DNA binding domain (the LexA DBD) could influence integration site selection, IN or IN fusions were incubated with linearized target DNA and a model viral DNA substrate. This substrate was a 16 mer/18 mer duplex with a "processed" end (the TT is removed, see FIG. 2). A PCR based assay was used to score for integration of model viral DNA substrate into a plasmid target (see Material and Methods). The target plasmid was pBR322 containing two tandem lexA operators inserted between the BamHI and SalI sites. Two PCR primers were used to detect integration events. One primer corresponds to a fixed site on the plasmid and the second primer corresponds to the viral sequence to be inserted. The size of the resultant PCR fragments corresponds to the distance from a fixed site on the plasmid to the integration site. It should be noted that this assay detects only insertion of what is equivalent to one viral DNA end, rather than the coordinated insertion event that takes place in vivo, involving the two ends of viral DNA.

Figure 3:
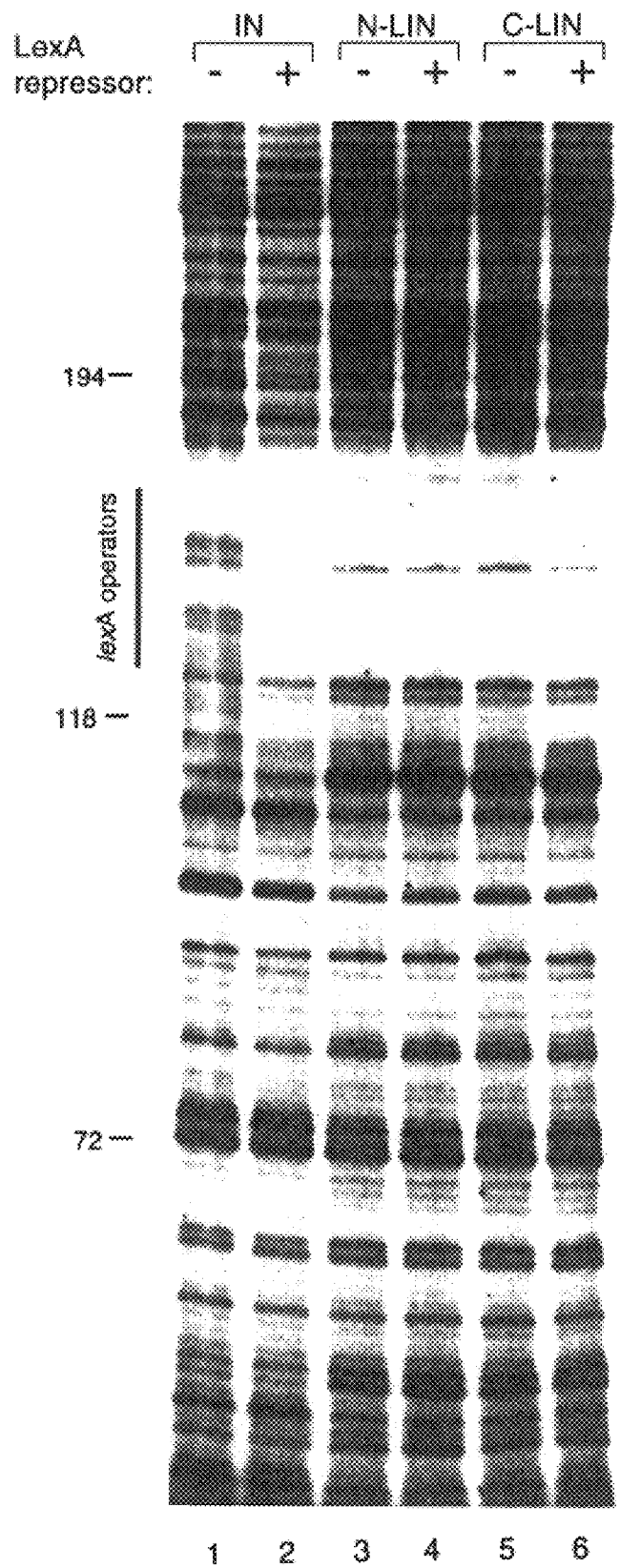
FIG. 3. Detection of in vitro integration events using a PCR-based assay. Labeled PCR products were fractionated on 7% polyacrylamide-urea sequencing gels. IN or IN fusions indicated above the lanes were incubated with the target plasmid containing the lexA operator segment depicted in FIG. 1B. The bands corresponding to integration sites within the lexA operators were determined by using the indicated size markers (indicated in base pairs) as well as a ten-base ladder (not shown). The estimated borders of this region are indicated on the left. Arrows indicate bands corresponding to enhanced integration sites associated with N-LIN and C-LIN proteins.

In the experiment shown in FIG. 3, the fixed PCR primer was ligated ca. 120 bp from the tandem lexA operators. The wildtype IN (lane 1) catalyzed integration into many sites and integration was not entirely random, as indicated by the varying intensities of bands. If purified LexA repressor proteins was added prior to the addition of IN, the lexA operator region became protected from integration events, indicating that the repressor is bound to the operators (lane 2). A general reduction in integration was also noted, which may be due to some nonspecific DNA binding of the LexA repressor protein. The patterns produced by N-LIN and C-LIN (lanes 3 and 5, respectively) were identical to each other, but differed from the pattern produced by wild type IN. Integration events within the lexA operator region were quenched. These results indicate that the fusion proteins were binding to the lexA operators and thus blocking integration of unbound fusion proteins into this region. The use of a neighboring integration site was tremendously enhanced in the case of both N-LIN and C-LIN (arrow). Significant enhancement of one other site closer to the primer was also noted (arrow). These results suggest that LexA DBD directs the N-LIN and C-LIN fusion proteins to the operator region and that the bound fusion proteins direct integration into nearby sites. Preincubation with equimolar amounts of LexA repressor protein was not sufficient to block this activity, indicating that the fusion proteins are tightly bound (lanes 4 and 6). One alternative explanation for the enhanced use of integration sites would be that the bound proteins distort the DNA helix in the vicinity of the operator and this may promote selective utilization of sites in this region. However binding of the complete LexA repressor protein to the operator has no such effect on wild type IN (FIG. 3, lane 2). Since tight binding to the operator requires dimerization of the LexA DBD, we also conclude that the IN portion of the fusion provides a dimer interface.

Interdomain flexibility may be required for selection of neighboring integration sites. The results in FIG. 3 suggested that LexA DBD-IN fusions were bound at the operator region and that this binding promoted use of neighboring integration sites. Since two of the N-terminal intra-domain fusions, LIN 18-286 and LIN 39-286, were active for processing and joining (FIG. 2), we used the PCR-based assay to assess their ability to target integration into sites adjacent to the operator. As controls, we assayed the corresponding deletion mutants, IN 18-286 and IN 39-286. The results shown in FIG. 4 indicate that the N-terminal deletions did not abrogate the ability of these proteins to direct integration into a heterologous target DNA (lanes 2 through 4). We therefore conclude that the complete ZF domain is not required for integration into a heterologous target DNA in vitro. However, the results indicate that, as compared to wild type, the deletions result in a slight reduction in integration activity, as well subtle variations in integration site selection (compare lane 2 with lanes 3 and 4). The corresponding LIN 18-286 and LIN 39-286 proteins displayed quenching of integration events in the operator region, indicating that these proteins are selectively bound at these operator sites (lanes 7 ad 8). However, the neighboring integration site (arrow) is no longer preferred as in cases of N-LIN or C-LIN (lanes 5 and 6). The LIN 52-286 and LIN 39-207 proteins showed no activity under these conditions (lanes 9 and 10), as might be expected from the results in FIG. 2. We conclude that fusion of the LexA DBD within the ZF domain results in a highly active protein which can bind to lexA operators; however fusion at the precise N-terminus allows the selection of preferred sites neighboring the operator. One interpretation is that the precise N-terminal (and C-terminal) fusions allows sufficient flexibility for the IN domain to access neighboring sites, while intra-domain fusion does not.

Figures 5A, 5B:
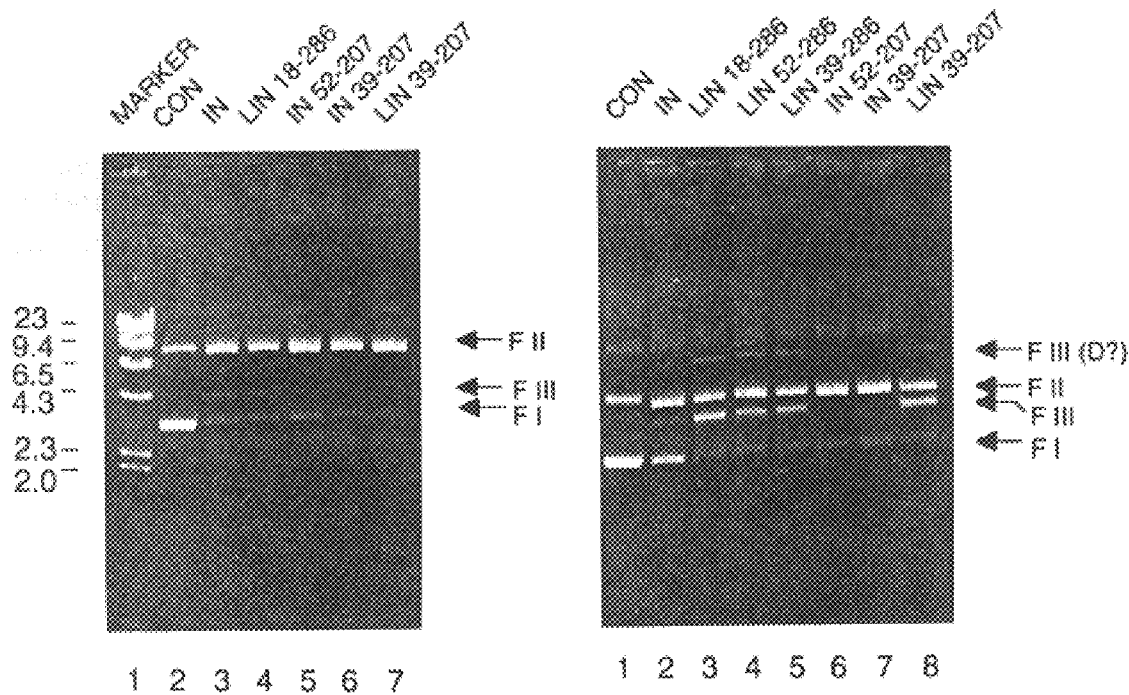

Targeting of IN endonuclease activity. We used a second approach to assess the selective binding and activity of the LexA DBD-IN fusions at the lexA operator site. With $Mn^{++}$ as a cofactor, ASV IN is able to nick and linearize supercoiled plasmids. This non-specific nicking seems to correspond to cleavage observed at the −3 site on the viral DNA substrates shown in FIG. 2. The biological relevance of this activity is unknown, but it requires the conserved residues in the catalytic domain. The supercoiled substrate shown in FIG. 5A is a pBR322 derivative lacking lexA operator sequences (lane 2). Two of the fusion proteins diagrammed in FIG. 1, LIN 18-286 and LIN 39-286, were incubated with this plasmid in the presence of $MnCl_2$ and the products were analyzed on an agarose gel (FIG. 5A, lanes 4 and 7, respectively). These fusion proteins, as well as wild type IN (lane 3) and the two non-fused catalytic domain fragments (lanes 5 and 6), all displayed similar levels of nicking activity as measured by production of form II (FII) and a small amount of linear form III DNA (FIII). These results confirm that the nicking activity maps to the ASV IN catalytic domain and is not affected considerably by various deletions and fusions. A similar experiment was carried out in FIG. 5B, except that the supercoiled substrate plasmid, pBRBSLexAOP, contained tandem lexA operators. Strikingly, the efficiency of linearization is much greater with the four proteins that contain the LexA DBD (FIG. 5B, lanes 3, 4, 5 and 8 as compared to wild type IN or the non-fused central domain fragments (lanes 2, 6 and 7). The linear product (FIII) appears to be formed at the expense of supercoiled substrate (FI) indicating concerted nicking. Although these assays are not highly quantitative, the selectivity for the operator is most pronounced when the IN 39-207 protein is compared to the corresponding LexA fusion protein, LIN 39-207 (FIG. 5B, lanes 7 and 8, respectively).

Figure 5C:
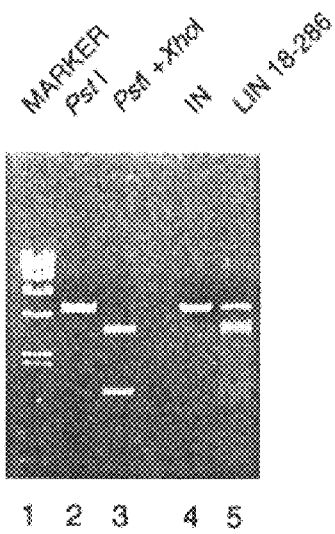
FIG. 5C: As in A and B, except that a PstI I-linearized version of the pBRBSLexAOP plasmid was used as a substrate. Markers for linearization at the lexA operator region were generated by cleavage with PstI and XhoI.

The results shown in FIGS. 5A and 5B suggest that the enhanced linearization of the operator-containing plasmids was due to preferential binding of the lexA-IN fusion proteins to the operator region, followed by localized concerted nicking. A linear substrate was used in order to map the preferred cleavage site in relation to a fixed site. The lexa operator-containing substrate was linearized with PstI, purified and then incubated with unfused IN or LIN 18-286. The results, shown in FIG. 5C, demonstrate that the LexA-IN fusion was able to preferentially cleave at or near the lexA operator, as indicated by generation of two discrete fragments of ca. 3400 bp and 1300 bp. These fragments migrated with the two marker fragments generated by cleavage with XhoI, which cleaves at the operator sites. All other LexA-IN fusions tested showed a similar profile on PstI-linearized substrates (data not shown). The bands produced by LIN 18-286 were somewhat heterogeneous, indicating that the ends might be frayed (FIG. 5C, lane 5). Fractionation of labelled DNAs on higher resolution gels confirmed that the termini produced by LIN 18-186 corresponded to many sites within, and flanking, the lexA operator region (data not shown).

As can be seen in FIG. 5C, lane 4, wild type IN does not produce any major uniform fragments from the linear DNA substrate, indicating that double strand breaks occur less frequently and less selectively. Interesting, when gels similar to that shown in FIG. 5C were probed after Southern blotting, the results indicated that the major site of double strand breaks produced by unfused IN also corresponded to the lexA operator region. We believe that the tandem array of palindromic operators may present a highly structured region of DNA which may be generally sensitive to nucleases and thus may enhance the detection of double strand breaks by both the fused and unfused IN proteins.

From these experiments, we conclude that the Mn-dependent nicking activity of the ASV IN catalytic domain can be directed to lexA operator sites by fusion with the LexA DBD and this results in site-specific double stranded breaks.

Figure 6:
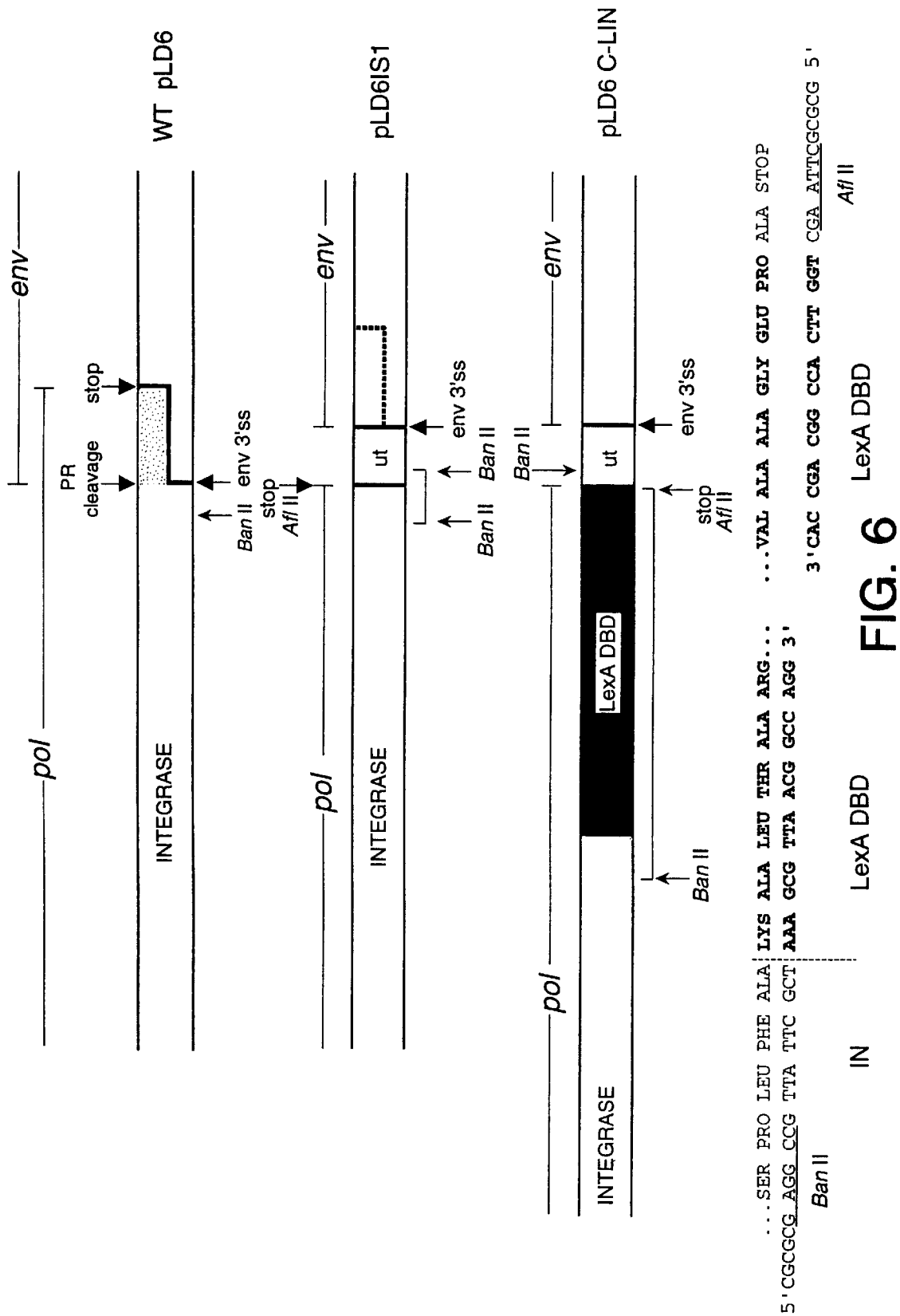
FIG. 6. Strategy for construction of an ASV genome encoding C-LIN. Top portion is a diagram of the env-pol overlap region of ASV. A small peptide of 37 amino acids (stippled region) is normally removed by the viral protease (PR) from the C-terminus of IN after assembly. The env 3'-splice site (ss) is indicated. Middle portion of the figure shows pLD6IS1, in which a stop codon has been introduced that corresponds to the proteolytic cleavage site and a noncoding spacer (nc) has been introduced between pol and env. Using pLD6IS1 as an intermediate, pLD6 C-LIN was constructed by inserting a PCR-generated LexA DBD coding fragment (hatched) between existing Ban II and Afl II sites. In the bottom portion of the figure, the two PCR primers are shown, along with amino acids encoded at the IN-LexA DBD junction (vertical dashed line) (amino acid sequence is Sequence I.D. No. 2, nucleotide sequence is Sequence I.D. No. 3) and at the new C-terminus of the C-LIN fusion (amino acid sequence is Sequence I.D. No. 4, nucleotide sequence from right to left is Sequence I.D. No. 5). Sequences in bold indicate LexA DBD coding sequences and corresponding amino acids.

The C-LIN protein is functional in vivo. One object of this invention is to influence, or re-direct retroviral DNA integration using a modified IN protein. Since the N-terminus of IN is fused to the RT in the gag-pol precursor in all retroviruses, it would be difficult to engineer a DBD (e.g. N-LIN) at this site in the viral genome. For example, a new viral protease (PR) site would have to be engineered in order to release the IN fusion from the gag-pol precursor. Also, in the case of ASV, IN exists as a domain of the RT $\beta$-chain, as well as a free peptide; thus, the heterologous DBD would likely interrupt folding of the RT $\beta$-chain. We therefore constructed an ASV DNA clone which encodes C-LIN, such that the DBD was tethered to the C-terminus of IN as well as to the C-terminus of the RT $\beta$-chain. This required re-engineering of the 3'-end of the pol gene in a manner which would not disturb cis-acting signals or overlapping coding regions. The same strategy was used to generate the bacterial expression construct and the relevant fragment was simply shifted to the viral DNA clone. Normally, the IN coding region partially overlaps with the env coding region (FIG. 6). The overlapping portion encodes a C-terminal ca. 4kDa peptide that is removed by the viral protease (PR) during virion morphogenesis and this peptide was shown to be nonessential (Katz & Skalka, 1988, supra). We therefore replaced the coding sequences for this peptide with the coding sequence for the LexA DBD. The cleavage site for PR should be destroyed by the fusion step. In order to preserve the intronic portion of the env splice acceptor site (which also overlaps with the IN coding region) we used a starting clone pLD6IS1 (Katz & Skalka, 1988, supra) which contains a noncoding spacer between env and po0 (FIG. 6, denoted nc). The spacer also contains a cis-acting suppressor mutation which was selected in vivo to maintain RNA splicing regulation.

Figure 7A:
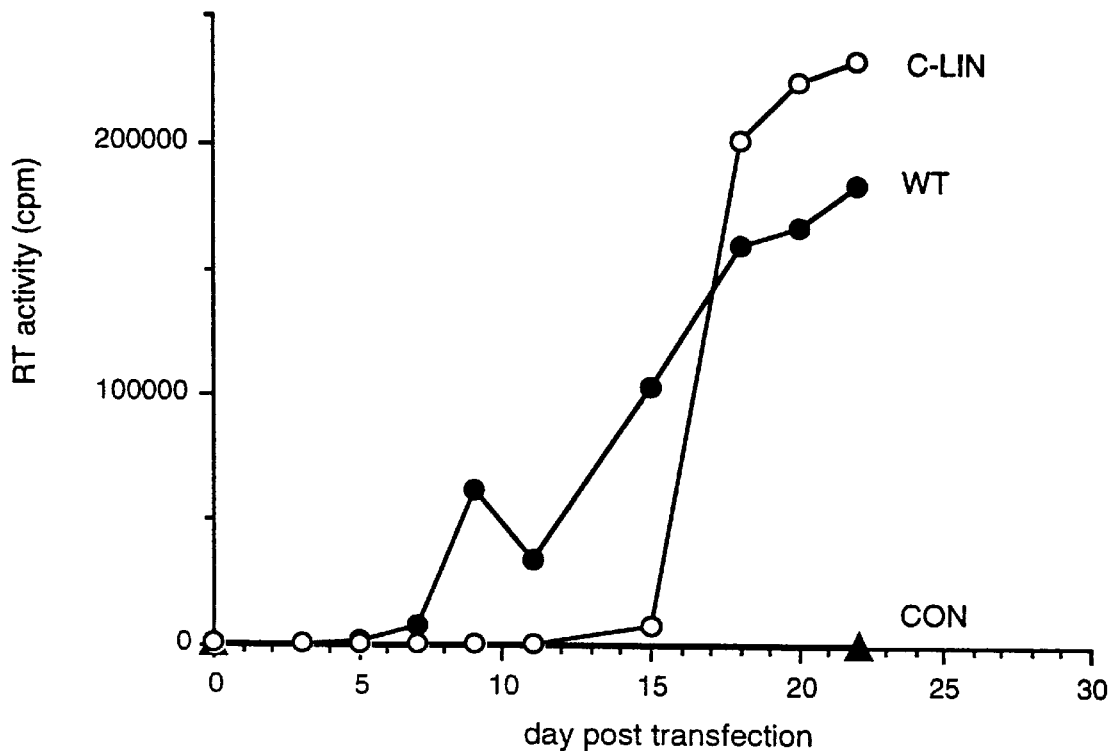
FIG. 7A: CEF cell were transfected with a wild type viral DNA pLD6 (WT) and the C-LIN construct pLD6IS1 C-LIN (C-LIN). Virus production was monitored by the reverse transcriptase assay. Control cultures (CON) were not transfected.

DNA transfection of susceptible chicken cells with the C-LIN viral construct resulted in the appearance of infectious virus (FIG. 7A). There was significant delay as compared to wild type, indicating that the alterations produced a replication defect. The delay was not due to use of the pLD6IS1 parent, since this virus replicates at a similar rate as wild type. These results indicated that viruses containing the additional IN domain have some replicative capacity; however the delay, followed by rapid appearance of infectious virus (between days 15 and 18) suggested the possibility of a genetic change that restored full replicative capacity. In comparison, replacement of the conserved carboxylates residues of the catalytic domain (FIG. 1) results in a complete block in ASV replication when assayed under similar conditions.

Figure 8A:
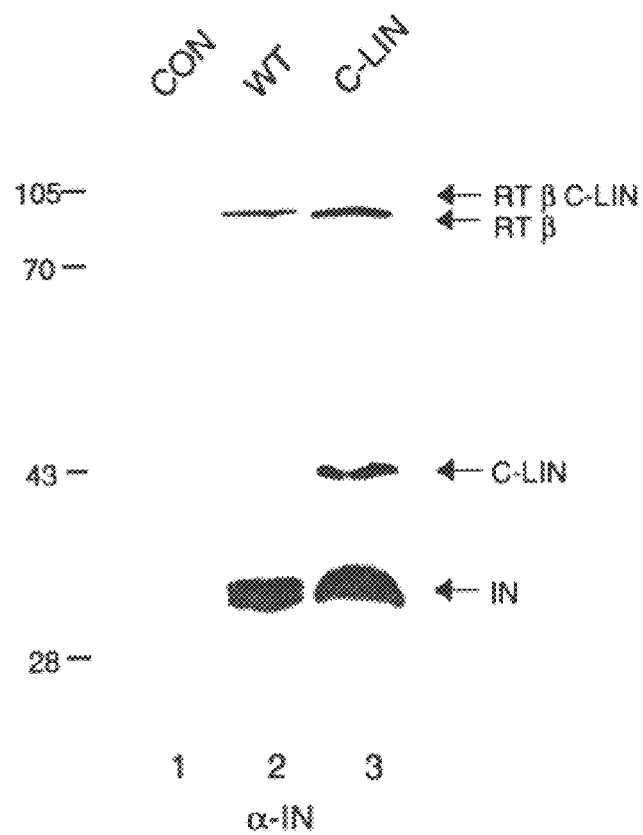
FIG. 8 (FIGS. 8A and 8B). Western blot analysis of virus collected at day 30 post transfection. The viral clone used for the original transfection is indicated above each lane (see FIG. 7). Virus particles were collected by pelleting and were applied to a 10% SDS-polyacrylamide protein gel. Western blots were probed with (FIG. 8A) anti-IN or (FIG. 8B) anti-LexA repressor protein rabbit polyclonal antibodies. The blots were developed with $^{125}$I-labeled protein G. Molecular weight markers (in megadaltons) are indicated on the left side of each panel.
Figure 8B:
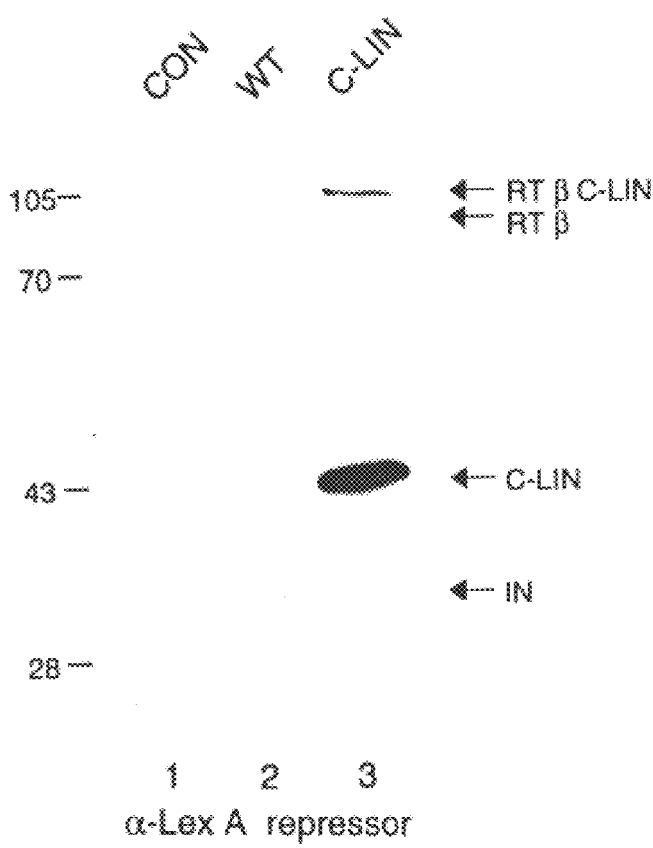

Western blot analysis (FIG. 8) using both anti-IN and anti-LexA repressor antibodies demonstrated that viruses from pLD6IS1 C-LIN-transfected cultures contained a mixture of C-LIN (ca. 42kDa) and IN-like proteins (32 KDa). At day 30 post transfection, the C-LIN to IN ratio was approximately 1 to 5 (FIG. 8A). As predicted, the LexA DBD is also detected on the $\beta$-chain of RT (FIG. 8B). In similar western blots from virus collected at earlier times (e.g., days 16 and 17) the C-LIN to IN ratio was approximately one-to-one (data not shown), suggesting a gradual loss of the LexA DBD. The free LexA DBD could not be detected in viral particles (data not shown) suggesting that the loss of this domain was the result of a genetic change, rather than proteolytic cleavage. To confirm the apparent genetic instability of the C-LIN virus, culture supernatant were collected at day 25 from the transfections shown in FIG. 7A, normalized by reverse transcriptase activity and then re-applied to fresh cells. As expected, virus collected from the C-LIN cultures now appeared at a similar rate to wild type. We note that the band corresponding to IN in the C-LIN-transfected cultures does not appear as the characteristic "doublet" of wild type IN. This observation suggests that the restored IN is not simply wild type and further analyses are under way. From these experiments we concluded that the C-LIN protein is produced in vivo and is assembled into virus particles. Although there is genetic selection against viruses that encode this domain, the C-LIN protein is likely functional in vivo (see Discussion) and is relatively stable.

DISCUSSION

The selection of retroviral integration sites is essentially random within host cell DNA, when catalyzed by a wildtype integrase. The evidence presented here demonstrates that IN can be augmented such that it is directed to a specified DNA sequence. This approach allows the study and use of IN molecules bound at a particular site on the DNA.

We have shown that fusion of the LexA DBD to either the N- or C-termini of ASV IN strongly influences integration site selection in vitro. The results are consistent with the binding of these fusion proteins to lexA operator sequences followed by enhanced the use of an adjacent integration site. The preferred integration site is located approximately one turn of the DNA helix from the lexA operator sites. Fusion of the LexA repressor to the precise IN termini appears to be important for preferential integration into neighboring sites. For example, LIN 18-286 and LIN 39-286 are active for integration and are also able to bind to operators (FIG. 4); however, these fusions do not preferentially select the neighboring integration site used by N-LIN (and C-LIN). One interpretation of these results is that there must be sufficient flexibility between the two fusion partners such that the neighboring integration site can be accessed. Interestingly, the intra-domain fusions LIN 18-286, LIN 39-286 and LIN 52-286 were able to selectively introduce double strand breaks within or adjacent to the operator region, indicating that the juxtaposition of domains is not critical for this activity (FIG. 5). Alternatively, the double-strand break assay may be inherently less quantitative and perhaps more sensitive.

The N-LIN and C-LIN fusions both selected the same preferred integration sites adjacent to the operators. This result suggests that these two fusions may be similarly positioned on the DNA, consistent with the notion that N- and C-termini are adjacent in the native IN structure.

The observation that all of the fusion proteins can be efficiently targeted to the operator region suggests that the IN domain provides a dimer interface. The LexA repressor normally binds to its cognate operator as a dimer, with the DBDs from each monomer contacting a "half-site" of the operator sequence (FIG. 1). The LexA repressor DBD (1-87) has been used extensively as a fusion partner to detect activation domains of transcription factors. To be efficient, the system requires that a multimerization domain be present. The positioning of the LexA DBD in relation to the dimerization domain is also important: the two DBDs in the dimer must be able to contact both halves of the operator simultaneously for high affinity binding. ASV IN functions as a multimer and biochemical mapping studies have indicated that self-association functions are contributed by both the catalytic domain and the C-terminal domain. Genetic analysis has also indicated that the catalytic domain of HIV IN contains a self-association function. The results presented here are consistent with the catalytic domain providing a dimer interface.

Figure 4:
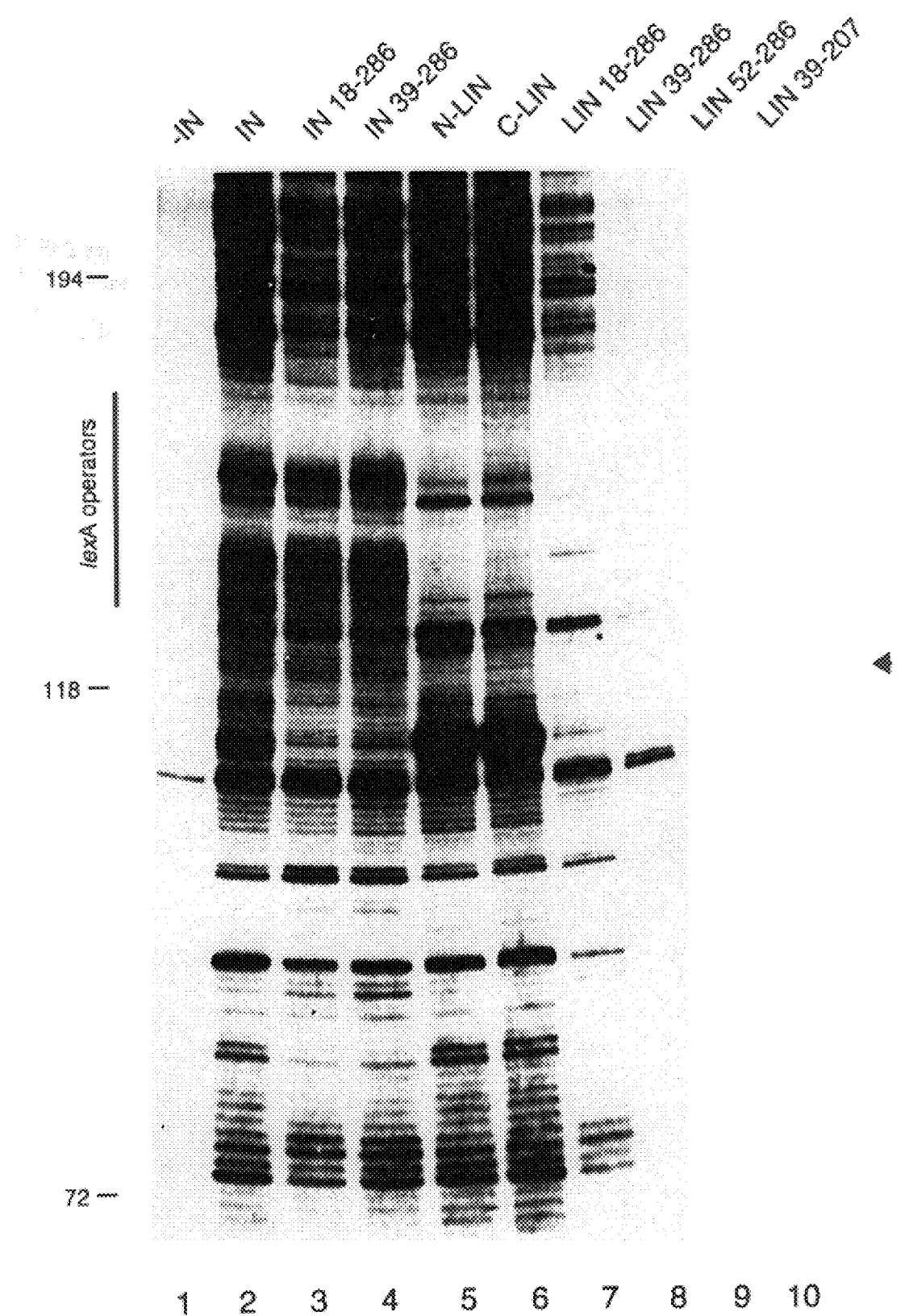
FIG. 4. Detection of in vitro integration events using a PCR-based assay. Proteins used in each assay are shown above. A control reaction was incubated without IN (lane 1,−IN). Symbols are as described in FIG. 3.

We also observed that fusion of the LexA DBD to positions 18 and 39 of ASV IN (LIN 18-286, LIN 39-286) resulted in retention of processing and joining activity, while fusion at position 52 (LIN 52-286) resulted in a severe reduction in activity (FIGS. 2 and 4). These fusions interrupt the conserved ZF domain. Although the isolated ZF domain does not bind to DNA, it has been implicated in DNA binding within the context of the whole IN protein. To determine if the LexA DBD might be complementing ZF domain function, we analyzed the corresponding deletion mutants (IN 18-286, IN 39-286). We find that these mutant proteins are also active, although their activity may be slightly reduced as compared to their fusion counterparts (FIG. 4). Thus, the ZF domain is not essential for processing or joining to a heterologous target DNA in vitro. Bushman and Wang (J. Virol. 68: 2215–2223, 1994) have reported similar results, except that the fusion of short heterologous peptides was required to complement the ZF deletion. We showed previously that the ASV ZF domain was not sufficient for DNA binding, although we did detect modest effects of single amino acid substitutions of either histidine 9 (H9) or histidine 13 (H13) residues (see FIG. 1) in the presence of $MgCl_2$. Here we show that the various ASV ZF deletion and fusion constructs are capable of catalyzing the insertion of model viral DNA ends into a heterologous target DNA in the presence of $MgCl_2$. $Mn^{++}$ is the preferred metal co-factor for ASV In in vitro and thus the use of the more biologically relevant, but less active, $Mg^{++}$ co-factor (FIGS. 3 and 4) provides a more stringent screen for the effects of these mutations. Although the ZF domain is not required in vitro, its conservation suggests that it does indeed have an important function. Substitution of ASV H9 or H13 produces a severe replication defect in vivo (not shown), which agrees with similar experiments in the HIV-1 system.

We provide evidence that all of the IN-LexA DBD fusions described here have varying degrees of selectivity for operator sequences. Although the relative binding of native IN versus fused IN was not directly measured, the results shown in FIG. 5 indicate an approximate 5–10 fold selectivity for introducing double strand breaks at or near the operator region. How might the LIN fusion proteins be arranged on the operator region to promote cleavage of both strands? Under limited nicking conditions, we observe many breaks focused within the operator region, but emanating to more distant sites. This suggests that IN or IN segments are able to make DNA contacts at some distance from the operator. The contact could be through aggregation of LIN molecules along the DNA or looping in of neighboring DNA sequences through binding to the catalytic domain. Although these possibilities cannot be distinguished from the experiments performed thus far, we generally believe that the enhancement of double strand breaks is the result of a high local concentration of LIN molecules at the operator region.

The fusion proteins described here enhance integration at a specific site, but integration events are not dependent on the operator sequences. Achieving absolute operator-dependent integration may require optimizing the arrangement of the IN dimer interface and the LexA DBD such that the cooperative interactions that occur between the native LexA repressor protein dimer and the operator can be fully reproduced. Greater selectivity might also be achieved by inactivating the IN domain that is normally responsible for binding to random host DNA. This non-specific DNA binding activity may map to the C-terminus of IN (Khan et al., Nucl. Acids Res. 19: 851–860, 1990) inasmuch as removal of this entire domain results in increased selectivity in the double strand break assay shown in FIG. 5 (LIN 39-207). Perhaps the arrangement of lexA operator sequences could also be optimized. In the experiments shown in FIGS. 4 and 5, we used two tandem operators that are in phase along the helix (FIG. 1). We speculated that this arrangement might promote higher order interactions between fusion dimers bound at each operator. It is possible that higher order IN complexes (e.g. tetrameres) are the active form for the joining reaction of the viral ends to target sequences and this tandem operator arrangement might increase IN activity by promoting such complexes. Although this hypothesis has not been systematically tested, we have found that single operators or tandem out-of-phase operators (such as used in FIG. 5) are sufficient for binding and double strand break activity, but not for the efficient, selective joining activities of C-LIN and N-LIN displayed in FIGS. 3 and 4.

Figure 7B:
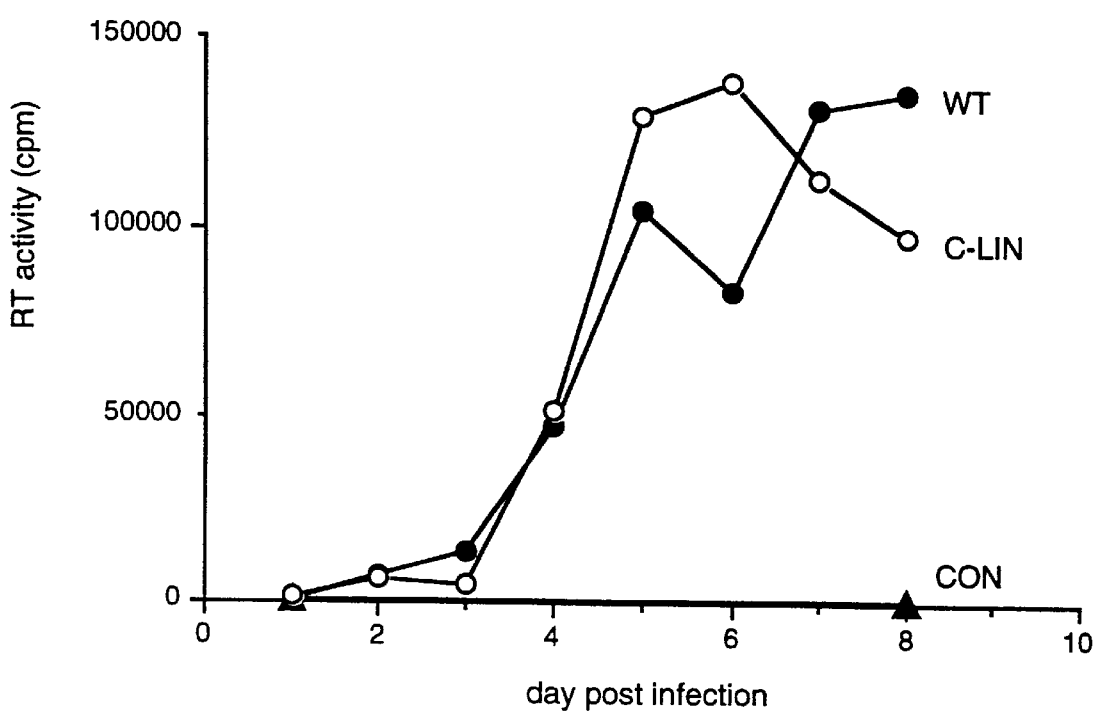
FIG. 7B: Supernatants collected on day 25 from FIG. 7A were normalized for RT activity and were applied to fresh CEF cultures. Control (CON) cultures were not infected. Virus production was monitored by the reverse transcriptase assay.

The fusion protein strategy we have described has also shown potential for targeting or enhancing retroviral integration in vivo. The C-LIN protein is highly active in vitro, is able to bind to lexA operators and promotes integration into nearby regions. We have also shown that it can be assembled into viral particles (FIG. 8), and our experiments indicate that the C-LIN fusion is active in vivo. Under our standard transfection conditions (FIG. 7), RT activity could not be detected unless multiple rounds of infection have occurred. For example, DNA transfection with an IN catalytic site mutant did not produce sufficient RT activity for detection (data not shown) because there was no significant amplification by cell-to-cell spread. Under our standard conditions, catalytic site IN mutants do not revert, presumably because this would require low-level replication. The results in FIG. 7 suggested that pLD6IS1 C-LIN virus was partially defective due to the presence of the extra IN domain, but could replicate sufficiently such that stabilizing mutations arose. Results of western blot analysis at early and late times support this interpretation. We conclude that the C-LIN protein is likely functional in vivo. We also considered the possibility that C-LIN molecules undergo proteolytic cleavage within the viral particle such that the LexA DBD is released and that the resulting nonfused IN is the biologically active form. However, we have not detected the expected ca.87 amino acid peptide in viral particles.

In summary, our results demonstrate the potential for augmentation of IN activity in vitro and in vivo. It can be postulated that an additional IN domain could also be used to target the retroviral pre-integration complex to protein components as well as DNA targets. The targeting and/or enhancement of retroviral integration should be extremely useful for basic research, to probe the interrelationship between various genes in complex gene expression pathways, as well as for gene therapy.

The present invention is not limited to the embodiments described above, but is capable of variation and modification without departure from the scope of the appended claims.

What is claimed is:

1. A nucleic acid molecule encoding a chimeric enzyme comprising a first segment derived from a first source operably linked to a second segment derived from a second source, said second source being different from said first source, said first segment encoding a DNA binding moiety and said second segment encoding an integrase moiety derivable from a retroelement, said integrase moiety having a carboxy terminus and an amino terminus, said amino terminus having a ZF domain, wherein said integrase moiety is truncated from said amino terminus so as to remove part or all of said ZF domain, and said DNA biding moiety is appended to said integrase moiety at said truncated amino terminus, said enzyme binding specifically to a targeted host DNA molecule having a characteristic determinant recognized by said DNA binding moiety, and possessing integrase activity, whereby said enzyme catalyzes site-specific integration of foreign DNA into a host genome sequence.

2. A vector comprising the nucleic acid molecule of claim 1.

3. The vector of claim 2, which is a retroviral vector.

4. A replication-competent retroviral vector comprising the nucleic acid molecule of claim 1.

5. The vector of claim 2, which is an expression vector selected from the group consisting of a procaryotic cellular expression vector, a eucaryotic cellular expression vector and a cell-free expression vector.

* * * * *